United States Patent [19]
Jordan et al.

[11] Patent Number: 6,080,412
[45] Date of Patent: Jun. 27, 2000

[54] PHARMACEUTICAL MICROENCAPSULATION

[75] Inventors: Olivier Jordan, Lausanne; Patrick Aebischer, Lutry; Jean-Francois Clemence, Weisendangen, all of Switzerland

[73] Assignee: Ecole Polytechnic Federale de Lausanne et al., Lausanne, Switzerland

[21] Appl. No.: 09/162,590

[22] Filed: Sep. 29, 1998

[30] Foreign Application Priority Data

Apr. 3, 1995 [GB] United Kingdom .................. 9506844

[51] Int. Cl.[7] ........................................ C07K 1/00
[52] U.S. Cl. ........................ 424/400; 424/450; 424/497
[58] Field of Search .................... 424/400, 450, 424/497

[56] References Cited

U.S. PATENT DOCUMENTS

| | | | |
|---|---|---|---|
| 4,921,757 | 5/1990 | Wheatley et al. | 428/402.2 |
| 5,091,187 | 2/1992 | Haynes | 424/450 |
| 5,437,274 | 8/1995 | Khoobehi et al. | 128/633 |
| 5,498,421 | 3/1996 | Grinstaff et al. | 424/450 |
| 5,820,879 | 10/1998 | Fernandez et al. | 424/450 |

FOREIGN PATENT DOCUMENTS

| | | |
|---|---|---|
| 2 172 104A | 9/1986 | United Kingdom . |
| WO 93/16687 | 9/1993 | WIPO . |

*Primary Examiner*—Thurman K. Page
*Assistant Examiner*—P. E. McQueeney
*Attorney, Agent, or Firm*—Ivor R. Elrifi; Mintz, Levin, Cohn, Ferris, Glovsky and Popeo

[57] ABSTRACT

A method of producing a microencapsulated pharmaceutical formulation is disclosed comprising causing a dye to be attached to the surface of pharmaceutical particles or particle clusters and applying a source of radiant energy to the dye in the presence of a liquid polymeric or polymerisable material so as to cause the material to cross-link, producing a conformal layer of cross-linked polymer on the particulate surfaces. Preferably, the polymer provides an immunoprotective layer around the particles, while allowing therapeutic components to exit the microcapsules. Microencapsulated pharmaceutical formulations and their medical use are also disclosed, especially for the treatment of diabetes by encapsulating insulin secreting cells.

20 Claims, 6 Drawing Sheets

Interfacial photopolymerization principle.

FIGURE 1: Interfacial photopolymerization principle.

FIGURE 2: Set-up for biological particles microencapsulation using an integrating sphere for homogeneous irradiation. Fiber feeding allows the use in a sterile environment.

FIGURE 3: Polymerization time as a function of the photosensitizer (Eosin Y) concentration.

FIGURE 4: Polymerization time as a function of the electron donor (TEOA) concentration.

FIGURE 5: Influence of the laser intensity on the polymerization time.

FIGURE 6: Influence of the PEG concentration on the polymerization time.

FIGURE 7: Pore diameter of PEG-based hydrogels computed from hydraulic permeability measurement.

FIGURE 8: Relative polymerization time of PEG-based photopolymer for different dyes.

FIGURE 9: Encapsulation with the eosin Y dye of (a) Langerhans rat islet showing a thick 50 μm coating in oblique illumination (bright zone below, dark zone above the islet)

(b) beta TC tet cluster, with a 20 μm coating.

(c) encapsulated rat islet using the eosin NCS dye (10 to 20 μm coating visible as a bright crescent above the islet, oblique illumination)

Islets have a mean diameter of 200 μm.

FIGURE 10: Viability assessment by calcein AM assay fluorescence of eosin Y impregnated, laser exposed Langerhans rat islets. Results shows a 100% viability for irradiation times of 10s.

FIGURE 11: Viability of encapsulated rat islet and FLPE stained islets exposed to laser during 90 s at 1W/cm$^2$ and 50 mW/cm$^2$.

PHARMACEUTICAL MICROENCAPSULATION

FIELD OF THE INVENTION

This invention relates to a method of microencapsulation, especially for pharmaceutical purposes. It is particularly applicable to the preparation of pharmaceutical formulations which comprise immunoisolated cells which produce and secrete therapeutic substances, eg insulin, and to the medical use of these formulations.

BACKGROUND OF THE INVENTION

Cell immunoisolation is a procedure which involves the placement of the cells or cell clusters within a semipermeable membrane barrier prior to transplantation in order to avoid rejection by the immune system. It can be applied to all cell types secreting a bioactive substance either naturally or through genetic engineering means. In practice, the main work has been performed with insulin secreting tissue. The molecular weight (Mw) cut-off of the encapsulating membrane can be controlled by the encapsulation procedure so as to exclude inward diffusion of immunoglobulins and lytic factors of the complement system, but allow the passage of smaller molecules such as glucose and insulin. The barrier permits therefore the β cell to respond physiologically to changes in blood glucose but prevents any contact with components of the immune system. Under these circumstances, xenogeneic tissue could be used, thus eliminating the supply problem, and no immunosuppression would be required to prevent rejection or disease recurrence since the grafted islets would be isolated from the host's immune system.

Early studies, which explored the immunoisolation principle using diffusion chambers to enclose islet tissue or pancreatic fragments, met with little success (reviewed in 1, 2). While transitory amelioration of hyperglycaemia was attained, available membrane materials did not permit prompt stimulus/secretion transport of insulin (3). More recently, the use of hollow capillary fibres in conjunction with allogenic or xenogeneic islets enclosed within a semipermeable chamber as an extracorporeal or intravascular insulin-secreting device has been successfully used for short term reversal of diabetes in rodents (4,5), dogs (6,7) and monkeys (8). The extracorporeal or intravascular approaches, although essential to prove the soundness of the encapsulation technique, are not fit for human applications especially in young children. Diffusion chambers—the method of choice for human applications—are, however, still hampered by consistency problems (9).

Several polymer capsule fabrication methods, based on different engineering techniques, have been developed. Encapsulation procedures are most commonly distinguished by their geometrical appearance, ie micro- or macro-capsules. In macro-encapsulation, cells or cell clusters are encased within permselective hollow fibres or flat sheet membranes. Since they are fabricated from thermoplastics, these capsules are mechanically stable and relatively easy to retrieve. Several investigators have reported the successful use of the thermoplastic based hollow fibre capsules to transplant islet cells in rodent models of diabetes. We have previously reported that, given appropriate surface microgeometry and chemical composition, the tissue reaction formed around implanted thermoplastic-based macrocapsules is minimal in both the brain (10) and the peritoneal cavity (11,12) of rodents. We have also reported long-term brain survival of macroencapsulated PC12 cells, a dopaminergic cell line, when transplanted across species (13) and that these implants significantly ameliorate behaviours in rat and primate (14) experimental Parkinsonian models. Using the same encapsulation system, Lacy and collaborators have reported the correction of streptozotocin-induced hyperglycaemia in rats implanted with subcutaneous macroencapsulated islet cells (15). More recently Scharp and collaborators have reported the 2 week survival of encapsulated human islets in diabetic patients using the same acrylic-based macro-encapsulation system (16). Using a similar acrylic system, we have recently reported the successful transplantation of bovine chromatin cells in the intrathecal space of humans suffering from terminal cancer pain. Explanted devices showed an absence of host reaction to the capsule as well as viable chromaffin cells. At retrieval, the capsules released catecholamine amounts comparable to those measured in vitro prior to transplantation. Although mechanically stable and biocompatible, hollow fibre based systems require a low packing density to allow for proper viability of the transplanted cells. The requirement to scale up this material system to correct diabetes in a human would require an impractical 50 m long device. Another limitation of this technique is the thickness of the capsule wall and its potential influence on glucose diffusion kinetics. The diffusion barrier may incur short-term hypoglycemic episodes due to excessive insulin secretion.

We have demonstrated that macroencapsulation using semipermeable hollow fibres is a viable technology for the xenogeneic transplantation of endocrine tissue in humans. Although this technology has also been used experimentally for the encapsulation and transplantation of islets, it is not appropriate for their effective packaging. The wall thickness of the capsules are usually a minimum of 100 $\mu$m and in the hollow fibre the cells are immobilized within a hydrogel matrix core typically 500–600 $\mu$m in diameter. This creates diffusion distances of several hundred $\mu$m between the host and the transplanted cells and may adversely effect diffusion kinetics. This diffusion-barrier may induce a significant "lag" time in detecting glucose levels within the blood that causes phase shifts in insulin secretion and therefore erratic regulation of blood levels glucose. Also, geometric constraints of the fibre technology result in very poor packing densities and may require up to several meters of transplanted islet encapsulated fibre.

One solution to these problems might be the use of the microencapsulation technique. In microencapsulation, cell clusters are immobilized in 500–600 $\mu$m hydrogel microspheres. Typically the semipermeable membrane is formed at the microsphere surface. Various chemical systems have been used. In the most common form, the capsule membrane is formed by ionic or hydrogen bonds between two weak polyelectrolytes; typically an acidic polysaccharide, such as alginic acid, and a cationic polyaminoacid, such as polylysine. Practically, the entrapment of cells is obtained by the gelation of a charged polyelectrolyte induced by exposure to a multivalent counter-ion. A counter-polyelectrolyte is then interfacially adsorbed on the cell immobilization matrix. Microcapsules possess an ideal shape for diffusion. In vitro tests demonstrated that insulin release from microencapsulated islets was equivalent to that from unencapsulated cells. They are, however, mechanically fragile, particularly when polyelectrolytes are used. They are also chemically unstable as they rely only on ionic bonds for integrity, leading to rupture of the microcapsules after several weeks of implantation into the brain of non-human primates. Intraperitoneal implantation of such microcapsules has been reported to reverse diabetes in rodent experimental diabetes models and more recently in humans. The poor biocompatibility of the system raises however questions about its use in young diabetes patients. In an effort to correct the stability and biocompatibility issue, Sefton and collaborators are developing microcapsules based on the precipitation of an organic polymer solution around islet clusters. Problems of solvent toxicity and evenness of the permeability characteristics still hamper this approach. In general, the use of microcapsule systems in humans is limited by problems of long-term stability and process limitations to ensure a uniform thin coating on a large volume of islets.

SUMMARY OF THE INVENTION

According to one aspect of the present invention there is provided a method of producing a microencapsulated pharmaceutical formulation; the method comprising causing a dye to be attached to the surface of pharmaceutical particles or particle clusters (herein referred to generally as "particles") and applying radiant energy to the dye in the presence of a liquid polymeric (or polymerisable) material so as to cause the material to cross-link, producing a conformal layer of cross-linked polymer on the particulate surfaces. Desirably the dye binds specifically to said surface (particularly to islet surfaces or cell membranes). Generally the dye s a fluorescent dye.

The cross-linking mechanism may involve laser induced excitation of the dye to its triplet state, creating free radicals from a suitable electron donor. These free radicals initiate polymer cross-linking resulting in hydrogel formation.

The "pharmaceutical" particles need not be directly pharmaceutical in effect, but may be for example cells or clusters of cells which produce and secrete a pharmaceutically active substance.

The polymer suitably provides an immuno-protective layer, ie one preventing the body's immune system from mounting an immune response to the particles, while allowing therapeutic components from the particles to exit the microcapsules. This is particularly appropriate where the particles comprise cells which produce and secrete a therapeutic substance such as a protein, the polymer being permeable to the therapeutic substance and to cell nutrients, but not of course to the cells themselves. The polymer is preferably a hydrogel, which can be cross-linked by irradiating the dye with a suitable energy source such as a laser, or becomes a hydrogel after the cross-linking. Typically the material prior to cross-linking contains polymer molecules, eg 400 g/mol–18500 g/mol.

The dye may be applied to the surface of the particles, by staining or other means, before contacting the thus treated cells with the liquid polymer (or polymer-forming) material, and exciting the dye to cross-link the polymer. The use of dyes specifically incorporated into the membrane allows us to restrict the diffusion phenomena, thus improving the coating thickness and reducing the phototoxicity. Alternatively, the material may be contacted with the particles simultaneously with the dye. For example, the molecules of the material (eg chains or micelles) may be labelled with the dye, and be capable of binding to the particles. For instance where the particles are cells, the material may be capable of binding the cell membrane, such as by amphiphilic interactions, by protein binding, or by other chemical means, or else by receptor-ligand or antibody-antigen interactions.

The polymer is cross-linked by excitation of the dye with an appropriate energy source, for example laser light of an appropriate frequency. The dye with the polymeric (or polymer-forming) solution and particulate material are suitably placed in a laser integrating chamber that ensures uniform polymerisation by equally distributing the laser light. The energy is supplied until a conformal coat of the desired thickness is formed around the material. By "conformal" coat is meant a thin coating which conforms to the shape of the material, eg the cells or cell clusters.

In a further aspect, the present invention provides a microencapsulated pharmaceutical formulation as obtainable by the above method.

In a further aspect of the present invention there is provided a pharmaceutical formulation in which a particulate pharmaceutical material is conformally coated with a polymer covalently cross-linked by the action of an irradiated dye.

In a further aspect, the present invention provides the abovementioned microencapsulated pharmaceutical formulations for medical use.

In a further aspect, the present invention provides the use of a microencapsulated pharmaceutical formulation comprising insulin secreting cells in the preparation of a medicament for the treatment of diabetes wherein the cells are conformally coated with a polymer covalently cross-linked by the action of an irradiated dye.

In a further aspect, the present invention provides an implant for the therapeutic regulation of glucose comprising microencapsulated particles as obtainable from the above method.

BRIEF DESCRIPTION OF THE DRAWINGS

FIGS. 1–11 depicts procedures and example of the claimed invention.

DETAILED DESCRIPTION

Our advance in encapsulation technology incorporates the advantages of both the micro- and macro-encapsulation techniques previously described. The mechanical stability of a covalently cross-linked hydrogel is combined with the biocompatibility and size of a microencapsulating hydrogel. A custom-designed laser polymerization process that individually coats cell clusters in large volumes with a permanently cross-linked hydrogel skin approximately 10 to 20 $\mu$m in thickness has been developed. The thin and uniform immunoisolating membrane is called a "conformal coating". This process allows a minimum glucose diffusion distance to the beta cells and a maximum packing coefficient for cell transplantation. Based on the assumption that 500,000 islet equivalents are necessary to reverse human diabetes, one can assume that 2 ml of conformally coated islets are required for therapeutic regulation of glucose.

Figure 1:
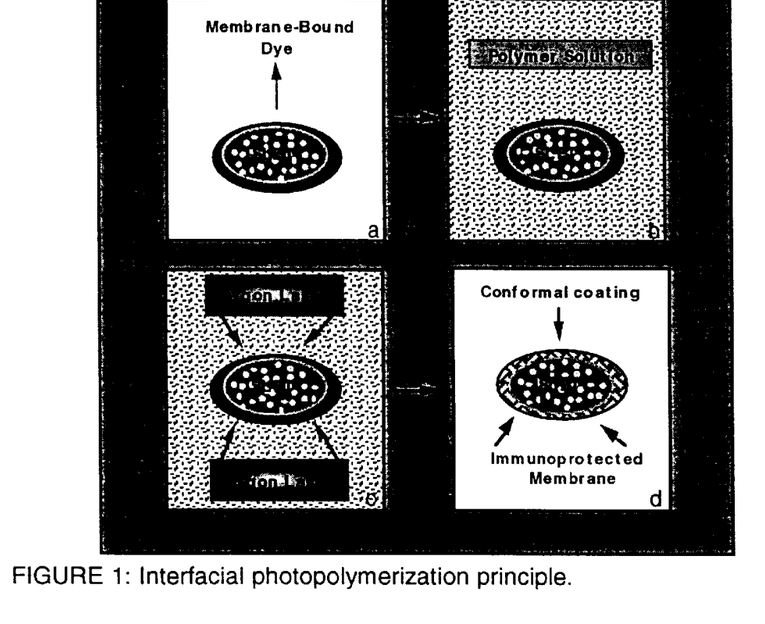
Figure 2:
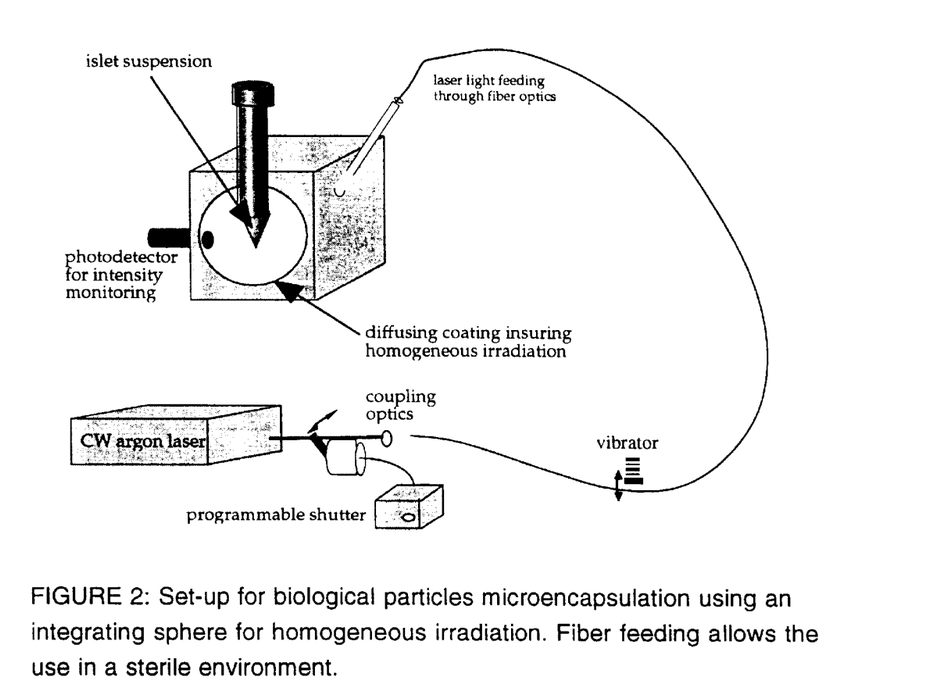

The conformal coat encapsulation methodology is illustrated in FIG. 1. The islets are first suspended in a solution composed of a fluorescent membrane staining dye. The membrane bound dye is an energy donor for the subsequent polymerization reaction. After staining, the islets are washed and resuspended in a polymeric solution that will readily polymerize into a hydrogel around the islets after excitation of the dye with an appropriate laser frequency. The islets are then placed in a custom designed laser integrating chamber (FIG. 2) that ensures uniform polymerization by equally distributing the laser light until a conformal coat of the desired thickness is formed around the suspended islets.

In preliminary experiments, we have studied the following conformal coat processing parameters:
a) Selection of a dye for specific staining of cell membranes Two kinds of dyes may be considered:
(i) Freely diffusing dyes, (e.g. eosin Y, eosin B, fluorescein, Rhodamine)
(ii) Dyes able to incorporate specifically into the cell membrane (e.g. DiI, D10, Isothiocyanate eosin, fluorescein and eosin derivatized phospholipids).
(i) Freely diffusing dyes:

Homogeneous Impregnations have been obtained using 1 mM eosin Y solutions. Impregnation times of 1 min to 10 min, followed by 1 or two washes were used. To visualize eosin absorption, confocal fluorescence microscopy was used on impregnated Langerhans rat islet and clusters of a beta cell line. It was shown that eosin Y was absorbed inside the cellular cytoplasm after 5 min of staining in a 1 mM solution.

(ii) Membrane staining dyes:

In order to reduce diffusion problems, we chose several dyes able to bind to cell membranes. The first two are cationic membrane markers belonging to the dialkylcarbocyanines family, DiI and DiO. Those amphiphilic markers interact with the double lipid layer. Eosin-5-isothiocyanate (eosin NCS) was also tested, which is know to bind to membrane proteins. Also, a fluorescein derivatized phospholipid (FLPE) appeared as a promising dye for microencapsulation. Langerhans rat islets and clusters of beta cell line have been impregnated with the above mentioned dyes. Confocal fluorescence microscopy has shown a fluorescent layer indicating a specific permanent adsorption of the dyes onto the membrane surface. FLPE Impregnation parameters were optimized. Impregnation times higher than 5 minutes and dye concentrations above 250 $\mu$M did not increase significantly the dye incorporation. The best results were obtained at a temperature of 4° C.

These encouraging results using specific staining open the way for new applications. An alternative way of controlling coating thickness would be the use of polymer chains or micelles, labelled with a dye, and owing one end group able to bind to the cell membrane. This binding can be achieved by amphiphilic interactions, by protein binding (as with the isothiocyanate group), or by other chemical ways. The dye absorption wavelength has to be fitted to the laser source—eosin or fluorescein for an argon laser. The length of the chains would allow the control of coating thickness, and high polymer molecular weight would prohibit membrane permeation, thus eliminating a possible phototoxic action. For example, an eosin labelled dextran, owing lipophilic or charged end groups, should fulfill the need for growing conformal polymer coatings.

Another way to achieve specific dye binding could be the use of immunochemistry, by coupling eosin to islet specific antigens. The specificity and the absence of membrane permeation would again permit conformal islet coating.
(b) Development of the photopolymer The polymer system used to conformally coat beta cells is a biocompatible polyethyleneglycol (PEG) based hydrogel. It consists of three elements: an aqueous solution of poly (ethyleneglycol 400 diacrylate) (PEG-DA) or poly (ethylene glycol 18 500 multiacrylate) (PEG-MA), the reaction initiator, triethanolamine (TEOA), and an appropriate dye acting as a photosensitizer (eosin Y, eosin NCS, FLPE, etc.).

Three process parameters need to be simultaneously controlled to form the thin uniform coating and ensure both its proper function as an immunoprotective membrane and its mechanical durability for processing and transplantation.

These parameters are the dye concentration, the amount of reaction initiator for polymerization, and the laser intensity, all optimized as a function of the reaction time. The reaction time was experimentally determined using an optical holographic technique for the PEG system[17,18]. A PEG photopolymer, contained in a quartz cuvette, is exposed to an interference pattern created by 2 intersecting argon laser beams (514 nm wavelength), thus writing a grating into the photopolymer. A low power He—Ne laser is used to probe the growth of this grating by measuring its diffraction efficiency. The polymerization time is defined as the time necessary to reach 90% of the maximum diffracted intensity.

Figure 3:
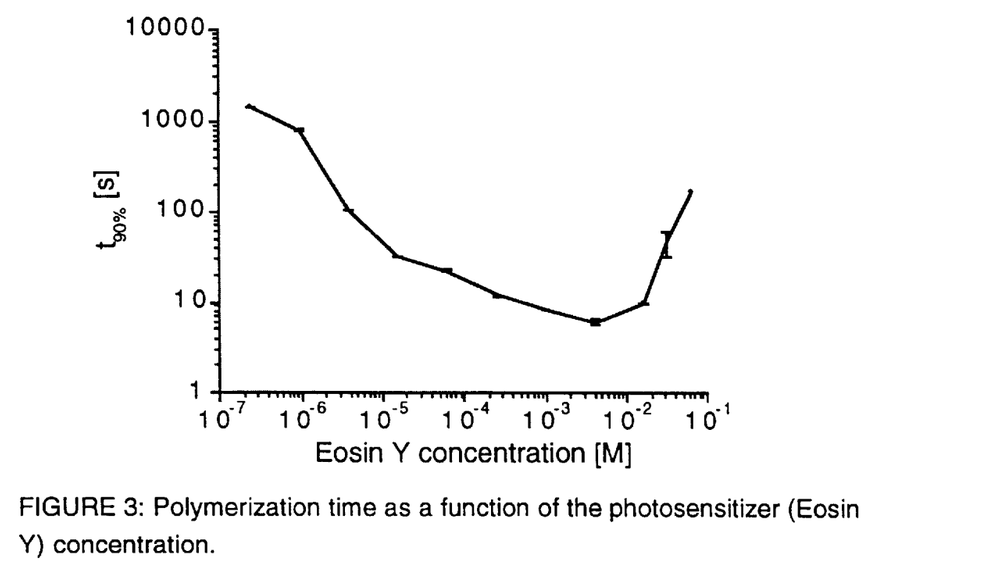

The dye concentration necessary to give a fast and complete polymerization reaction at a maximum laser intensity of 1 W/cm$^2$ was first determined. The TEOA concentration of 90 mm used was not a limiting factor of the reaction speed. The FIG. 3 displays the polymerization time as a function of the eosin Y concentration for a 10 $\mu$m thick film. An optimum concentration, corresponding to 70% of light absorption through the film, is demonstrated. Higher[11] dye concentrations lead to inhomogeneous polymerization due to incomplete dye bleaching. From these measurements, 1 mM dye concentration were used for cell microencapsulation.

Using the optimized dye concentration and an irradiation intensity of 1 W/cm$^2$, the minimum reaction initiator TEOA concentration necessary to complete polymerization was determined. In this way, a minimum quantity of non-consumed monomer TEOA will remain after polymerization.

Figure 4:
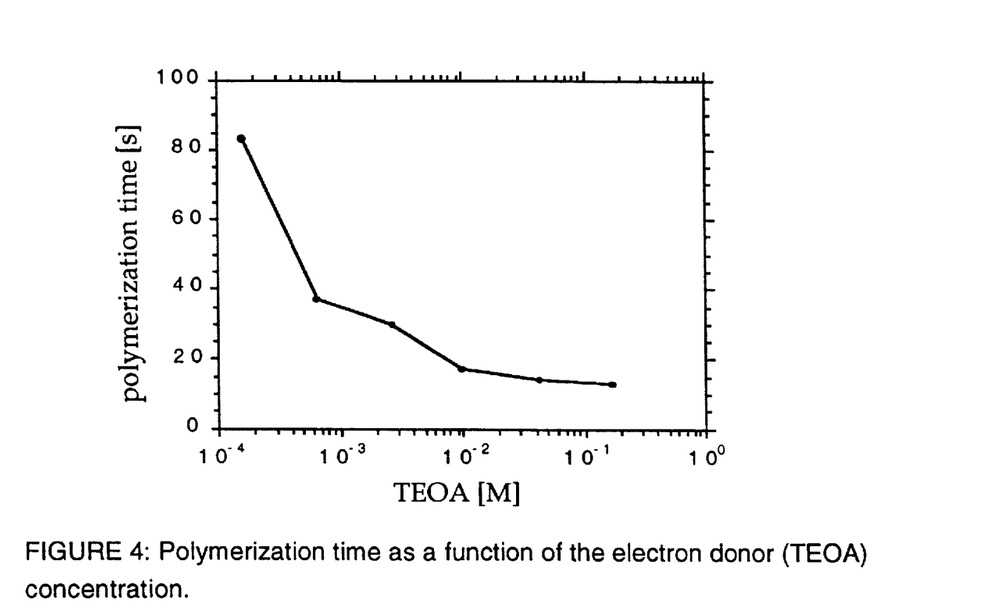

FIG. 4 shows the influence of the TEOA concentration on the polymerization time. A concentration of at least 90 mm was required to maximize reaction speed.

Figure 5:
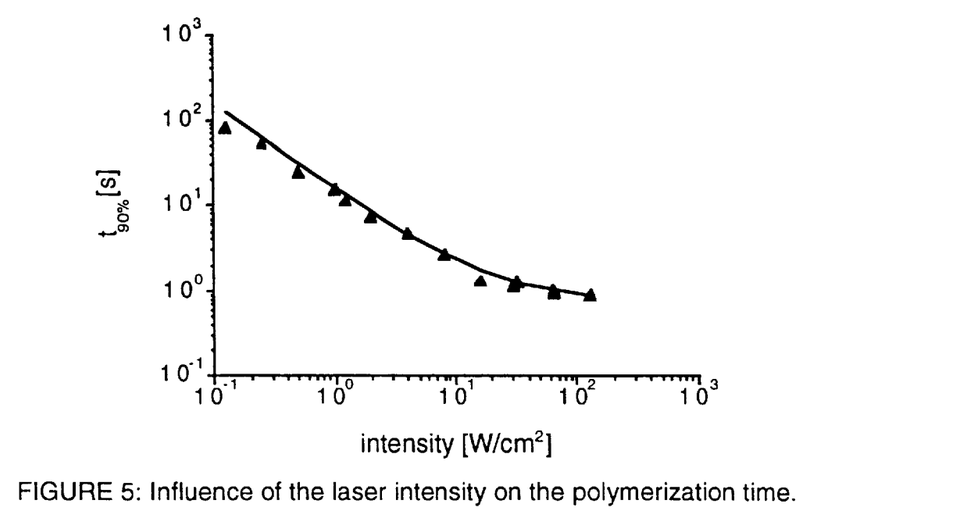

The irradiation time necessary for the photopolymerization was determined using the optimized reaction parameters. FIG. 5 shows the relationship between polymerization time and laser intensity. For example, a laser intensity of 1 W/cm$^2$ during 13 seconds were necessary to complete polymerization.

Figure 6:
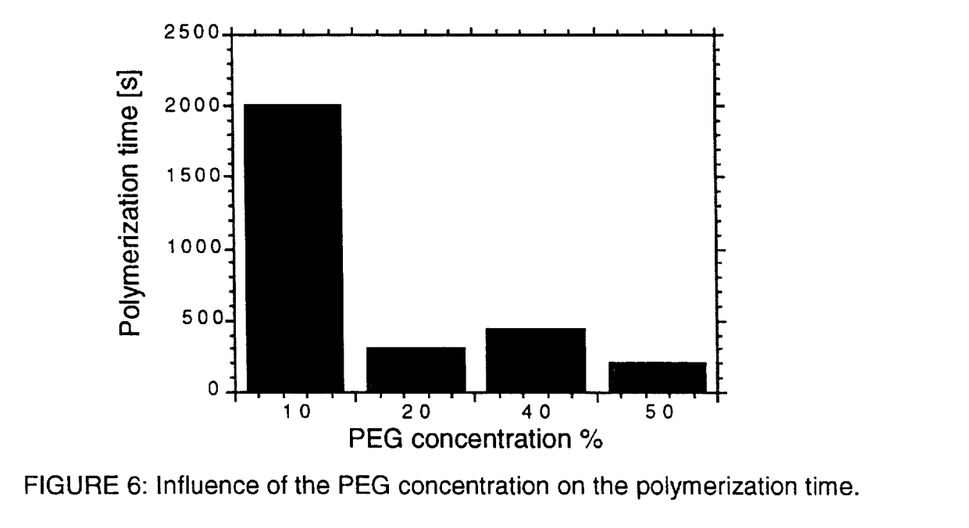
Figure 7:
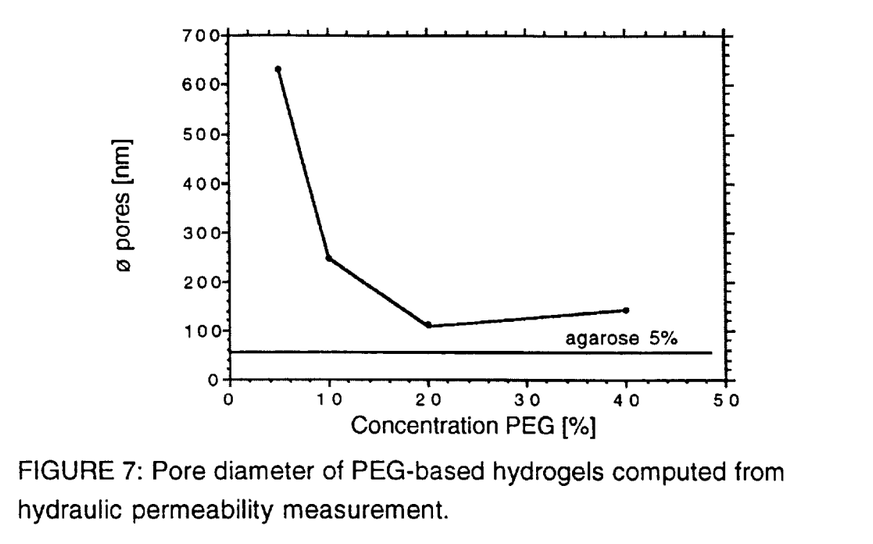

The use of a low PEG-DA concentration (10% (w/v) concentration into physiological medium) resulted in a very low reaction speed (FIG. 6). Moreover, the gels obtained were mechanically fragile, and showed a higher permeability to water than a 5% (w/v) concentrated agarose gel (FIG. 7). Based on these measurements, PEG concentrations of 20% to 30% were used.

Figure 8:
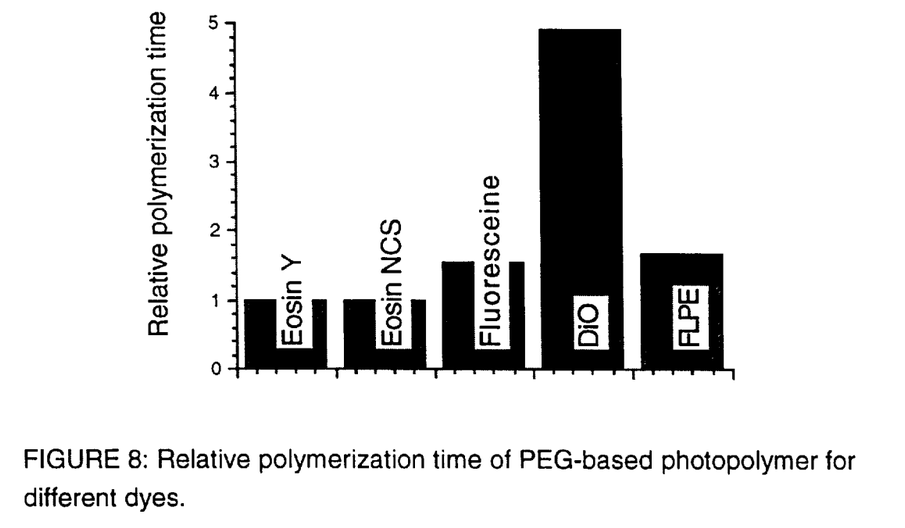

From a photochemical point of view, the dyes mentioned in section a) were very different. Measurements of photopolymerization speed by the holographic technique gave irradiation times of 17 minutes for DiO and 10 minutes for DiI (see FIG. 8). Eosin NCS was 1.4 times slower than eosin Y. This behaviour can be explained by the eosins high triplet conversion efficiency, allowing high reaction quantum yield. FLPE induces photopolymer cross-linking in twice the time necessary for eosin Y. Other dyes have also proven to be efficient photosensitizers, eg eosin B, rose bengal and stilbene.

c) Encarsulation of biological cell clusters
(i) Encapsulation with freely diffusing dyes:

Microencapsulation of Langerhans islets has been previously reported[19,20]. Encapsulation was assessed using the eosin Y photosensitizer. Primary cells (Langerhans rat islets) and a genetically engineered mouse beta cell line (beta TC tet) have been successfully encapsulated (see FIG. 9(*a*) and (*b*)). A PEG-DA solution of 3.0% (w/v) containing 90 mM TEOA was used, and islets were impregnated in a 1 mM eosin Y physiological solution for 5 min. The irradiation intensity was 1 W/cm$^2$ during 20 s. Coating thicknesses of 50 $\mu$m down to 20 $\mu$m were obtained. It has been shown that the coating thickness can be controlled by both the irradiation time and the polymer concentration. Longer irradiation times resulted in thicker coating due to dye diffusion, whereas higher polymer concentration resulted in thinner coating due to the increased viscosity. However, two major drawbacks arised; firstly, the intake of the dye inside the cells lead to toxicity due to photogeneration of free radicals. Secondly, sedimentation and convection generated non uniform flows around the islet, resulting in irregular coatings (formation of tails) and may lead to mass polymerization of the polymer solution. To overcome these problems, specific membrane staining dyes have been demonstrated for microencapsulation.

Figure 9:
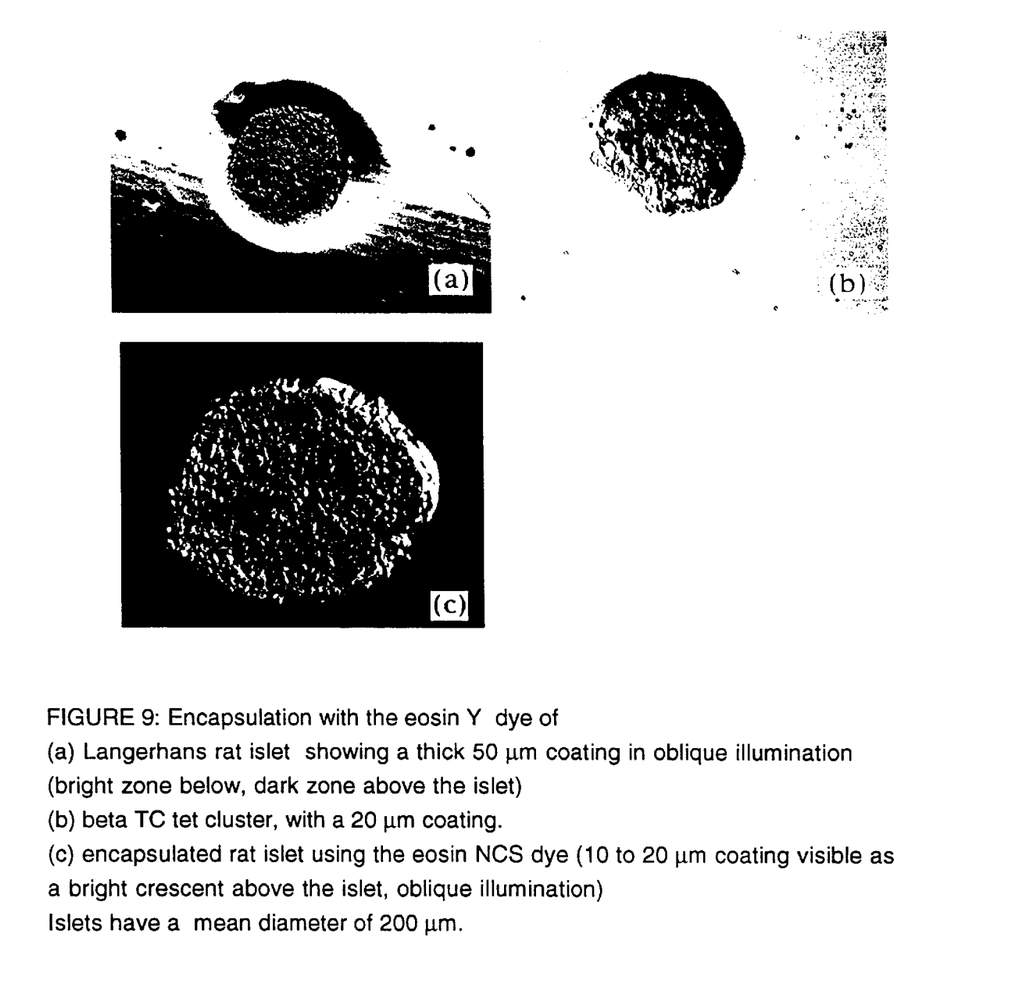

(ii) Encapsulation with membrane staining dyes:

Staining of Langerhans rat islets was done in a 1 mM eosin NCS solution. Due to the low kinetics of incorporation, long impregnation times (up to 2 hours) were necessary. After two washes in saline solution and resuspension in the PEG-DA 30% (w/v) polymer solution, islets were irradiated with intensities ranging from 100 mw to 1 W/cm$^2$ during 10 to 30 s. Conformal coatings with thicknesses of 10 to 20 microns were obtained. In a single suspension, about 80% of the islets were encapsulated with a visible coating surrounding the whole islet (see FIG. 9(c)). Comparative encapsulation experiments gave better results with the membrane-bound eosin NCS dye than with the eosin Y, giving a thinner conformal coating, without the "tail effect". The tendency to induce mass polymerization of the islet solution was also reduced. Maintaining these encapsulated islets in culture showed that they survive the photopolymerization process. Further studies are needed for assessing full islet functionality.

These experiments demonstrated that the use of membrane bound dyes for the microencapsulation of biological particles allows to reduce coating thickness, thus giving faster kinetics of release.

New dyes are currently under investigation. Fluorescein derivatized phospholipids as fluorescein DHPE (FLPE) has been shown to bind specifically to the cell membrane and to induce polymerization with a high efficiency. Eosin DHPE can also be used, its high triplet state efficiency leading to efficient photopolymerization.

d) Toxicity of the process

During the microencapsulation process, biological particles are placed in conditions far from those of a biological media. Damages of chemical, thermal, mechanical or photochemical nature may limit cell viability or functionality. Cell viability is measured by a vital stain fluorescence method (fluorescein diacetate (FDA) or calcein AM assays), and functionality is assessed by dynamic measurement of insulin secretion under glucose stimulation.

Chemical toxicity assessment was achieved by incubation of Langerhans islets to the pre-polymer solution (PEG-DA 30% (w/v) and TEOA 90 mM). Islets have shown a 100% viability up to an incubation of 4 minutes. As the microencapsulation process lasts about 30 s, no chemically induced damage is expected from the pre-polymer. Toxicity of the dye impregnation has also been verified. No chemical toxicity has been measured for eosin Y and FLPE n the staining condition mentioned above. However, eosin NCS has been shown to inhibit insulin secretion after 10 min impregnation in a 1 mM solution.

Cell clusters are extremely sensitive to mechanical stress. Desegregation of cell clusters has been reported after exposure to a shear stress of 5 N/m$^2$ during 10 s. These kind of shear stresses are readily obtained[21] in other microencapsulation processes as micro droplet extrusion through nozzles. In the interfacial polymerization process, almost no shear stress occurs. No cell desegregation has been seen during our encapsulation experiments.

Heating of the cell clusters caused by the absorption of laser light or the heat of polymerization may damage cell tissues. Computer calculations have shown that in the photopolymerization conditions used (e.g. intensity lower or equal to 1 W/cm$^2$, 1 mM dye concentration, 10 to 30 s polymerization) a maximal temperature increase of 1.4 degrees is expected. As a consequence, no damage is expected from laser-induced heating.

Figure 10:
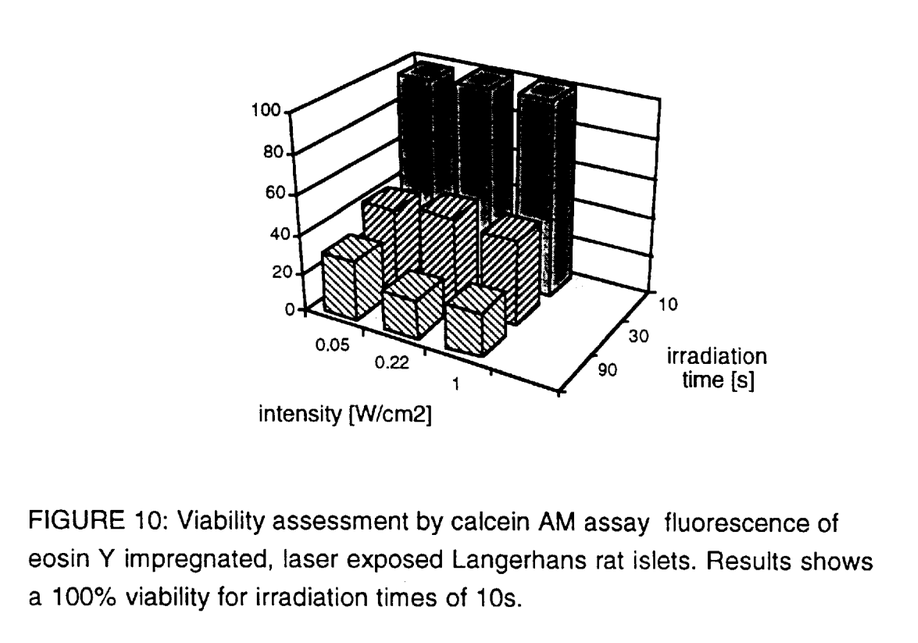

Phototoxic effects may result from de-excitation of dyes via generation of toxic free radicals. Assessment of this effect on cell viability is shown on FIG. 10. Langerhans rat islets, impregnated with a 1 mM eosin Y solution, were exposed to various laser irradiation intensities and times, and viability was measured after one day. Viability of 100% was measured for 10 s irradiation times and laser intensities ranging from 50 mw/cm$^2$ to 1 W/cm$^2$. Longer irradiation times lead to a decreased viability, along with a reduced insulin secretion. Thus irradiation times below 30 s have to be used for the microencapsulation process.

Figure 11:
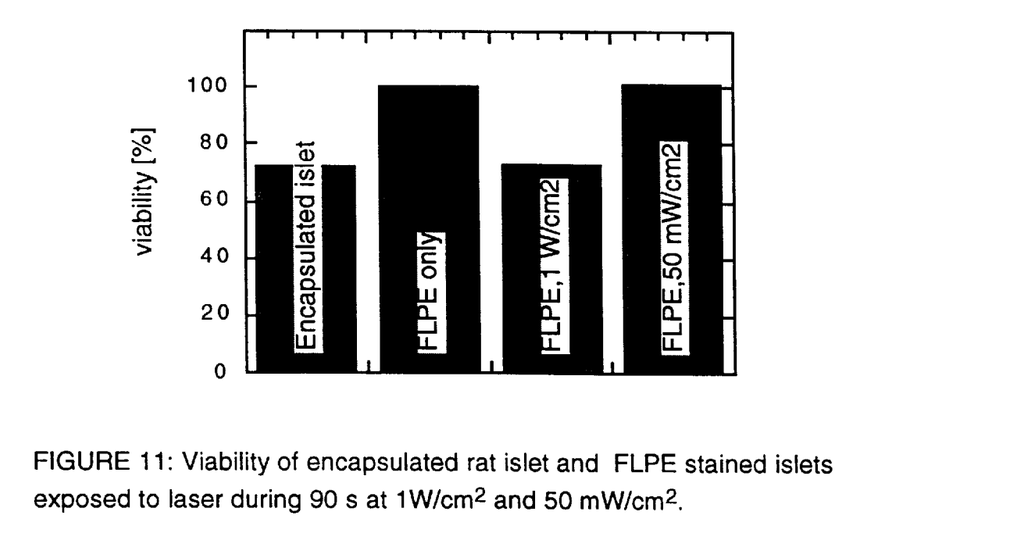

Viability of FLPE stained, laser exposed rat islets was measured (see FIG. 11). After staining in 200 µM FLPE solutions during 75 min at 4° C., a viability of 100% was obtained at an irradiation intensity of 50 mW/cm$^2$, and 70% at 1 W/cm$^2$. These results turns FLPE dye into a promising photo initiator for microencapsulation.

Viability of encapsulated Langerhans rat islets was also assessed. After encapsulation in a PEG-DA 30% membrane using a 1 mM eosin Y concentration and a 10 s irradiation at 1 W/cm$^2$, a viability of 70% ±10% has been measured (mean over eight samples±standard deviation). This latter result implies that low damage to the cell membrane occurs during the whole microencapsulation process.

e) Development of a photo-activated hydrogel based on benzophenone chemistry

A second material encapsulation technology using heterobifunctional linkers based on benzophenone chemistry (BP) will be developed. The advantage of this chemical technology is its ability to effectively cross-link practically any hydrogel material. BP chemistries are light activated in the near UV range (350 nm) and will readily react with C—H bonds. In preliminary experiments we observed that islet cells could tolerate exposure to 100 mW per cm$^2$ for several minutes. BP chemistries can be custom designed so that one end thermochemically reacts to a specific chemical functional group and the other end containing the BP chemistry can then be photo-activated to initiate a cross-linking reaction. The BP chemistry can also be effectively utilized within an aqueous environment. In collaboration with Dr H Sigrist of the University of Bern, our laboratory has developed a bifunctional linker that can be thermochemically derivatized onto albumin with the BP unit on the other end available for photo-crosslinking. The albumin-BP could prove an ideal system for conformally coating a polymeric skin around the β-cell clusters. This can be accomplished by first adsorbing the albumin-BP onto the β-cells and then photo-activating the β-cells in a hydrogel solution. In this way, the adsorbed albumin-BP on the cell membrane will be immediately fixed while simultaneously crosslinking a hydrogel skin around the β-cell clusters. The albumin-BP can be produced in large quantities and tried on a beta cell line for comparison with the previously described interfacial polymerization reaction.

The derivatization of a phospholipid, for example phosphatidylethanolamine (PE), with BP chemistry will also be evaluated. If this is accomplished, the lipid can be effectively incorporated within the membrane and the BP chemistry can then be activated to photopolymerize any hydrogel system around the islet aggregates. The advantage of using a dye compared to the derivatized albumin is the proximity and immobilization of the dye within the membrane compared to the adsorbed albumin system. The polymeric "skin" formed by the BP activation affixed to the membrane dye may form a thinner more tightly bound hydrogel membrane.

Several hydrogel based systems will be experimentally tested for cross linking with the BP chemistry. These include pure PEG, polyvinyl alcohol and agarose. These hydrophilic systems are known to be highly biocompatible as they show the lowest protein adsorption and therefore prevent any significant cell adhesion. These cross-linked hydrogels may prove especially interesting as they should show improved mechanical and chemical stability compared to the polyelectrolyte systems currently used for transplantation studies.

REFERENCES

1. Hegre, O. D. Islet cell transplantation in "The Diabetic Pancreas", eds. Volk and Arquilla, Plenum, New York, 1985.
2. Tze, W. J. and Tai, J.: Manipulation of pancreatic islet cells in allotransplantation. Trans Proc. 14:714, 1982.
3. Theodoron, N. A., Vrbova, H., Tyhurst, M., and Howell, S. L.: Problems with the use of polycarbonate diffusion chambers for syngenic pancreatic islet transplantation in rats. Diabetologia 18:313, 1980.
4. Chick, W. L., Perna, J. J., Lauris, V., Low, D., et al: Artificial pancreas using living beta cells: effects of glucose homeostasis in diabetic rats, Science 197:780, 1977.
5. Tze, W. J., Wong, F. C. and Chen, L. M.: Implantable artificial capillary unit for pancreatic islet allograft and xenograft, Diabetologia 16:247, 1979.
6. Tze, W. J., Tai, J., Wong, F. C., Davis, H. R.: Studies with implantable artificial capillary unit containing rat islets on diabetic dog. Diabetologia 19: 541, 1980.
7. Sullivan, S. J., Maki, T., Borland, K. M., Mahoney, M. D., Solomon, B., et al Biohybrid artificial pancreas; long-term implantation studies in diabetic, pancreatectomized dogs. Science 252: 718, 1991.
8. Sun, A. M., Parisius, W., Healy, G. M., Vacek, I., et al: The use in diabetic rats and monkeys of artificial capillary units containing cultured islets of Langerhans. Diabetes 26:1136, 1977.
9. Colton, C., Avgoustiniatos, E. S. Bioengineering in development of the hybrid artificial pancreas. J. Biomech. Eng. 113:152, 1991.
10. Winn, S. R., Aebischer, P., Galletti, P. M. Brain tissue reaction to permselective polymer capsules. Biomed. Mater. Res., 23: 31, 1989.
11. Christenson, L., Aebischer, P., McMillan, P., Galletti, P. M. Tissue reaction to intraperitoneal implants: species difference and effects of corticoid and doxorubicin. J. Biomed Mater. Res., 23: 705, 1989.
12. Christenson, L., Wahlberg, L., Aebischer, D. Contribution of mast cells to tissue reaction to intraperitoneally implanted polymer capsules and effect of local release of corticoid. J. Biomed. Mater. Res., 25: 1119, 1991.
13. Aebischer, P., Tresco, P. A., Winn, S. R., Greene, L. A., Jaeger, C. B. Long-term cross-species brain transplantation of a polymer-encapsulated dopamine-secreting cell line. Exp. Neurol. 111: 269, 1991.
14. Tresco, P. A., Winn, S. R., Tan, S., Jaeger, C. B., Greene, L. A., Aebischer, P. Transplantation of polymer encapsulated PC12 cells reduces lesion-induced rotational behaviour. Cell. Transpl., in press.
15. Lacy, P. E., Hegre, O. D., Gerasimidi-Vazeou, A., Gentile, F. T., Dionne, K. E.: Maintenance of normoglycernia in diabetic mice by subcutaneous xenografts of encapsulated islets. Science 24:1782, 1991.
16. Scharp, D. W., Lacy, P. E., Santiago, J. V., McCullough, C. S., et al. Results of our first nine intraportal islet allografts in type 1, insulin-dependent diabetic patients. Transpl. 51:76, 1991.
17. Jordan, O. and Marquis Weible F., "Holographic control of hydrogel formation for biocompatible photopolymer", 2629: 46 (1995).
18. Jordan, O. and Marquis Weible F., "Characterisation of photopolymerisation by holographic technique applied to a diffuse hydrogel", submitted to Applied Optics (1995).
19. Sawhney A. S., Pathak C. P. and Hubbell J. A., "Modification of islet of Langerhans surfaces with immunoprotective poly(ethylene glycol) coatings via interfacial photopolymerisation", Biotech. Bioeng. 44: 383–386 (1994).
20. Hubbell J. A., U.S. Patent WO93/16687 PCT/US93/01776, 1993
21. Hua J. M., Erickson L. E, Ylin T. Y. and Glasgow L. A., "A Review of the Effects of Shear and Interfacial Phenomena on Cell Viability". Crit. Rev. Biotech. 13: 305–328 (1993).

What is claimed is:

1. A method of producing a microencapsulated pharmaceutical formulation, the method comprising causing a dye, wherein the dye is derivatized with phospholipid, to be attached to the surface of pharmaceutical particles or particle clusters and applying a source of radiant energy to the dye in the presence of a liquid polymerisable material selected from the group consisting of polyethylene glycol and acrylate copolymers thereof so as to cause the material to cross-link, producing a microcapsule having a conformal layer of cross-linked polymer on the surface of the pharmaceutical particles or particle clusters.

2. The method of claim 1 wherein the polymer provides an immunoprotective layer, while allowing therapeutic components from the pharmaceutical particles or particle clusters to exit the microcapsules.

3. The method of claim 2 wherein the pharmaceutical formulation further comprises cells or clusters of cells which produce and secrete a pharmaceutically active substance.

4. The method of claim 3 wherein the polymer is permeable to cell nutrients.

5. The method of claim 1 wherein the dye is excited to a triplet state when irradiated by the source of radiant energy, which excitation leads to the formation of free radicals which initiate cross-linking.

6. The method claim 1 wherein the dye is capable of binding to the surface of the pharmaceutical particles or particle clusters.

7. The method of claim 6 wherein the dye is selected from the group consisting of eosin derivatized phospholipids or fluoroscein derivatized phospholipids.

8. The method claim 1 wherein the polymerisable material is a hydrogel which can be cross-linked by irradiating the dye with a laser which can produce light of an appropriate frequency.

9. The method of claim 1 wherein the dye is applied to the surface of the pharmaceutical particles or particle clusters before contacting the pharmaceutical particles or particle clusters with liquid polymerisable material and energising the dye to cross-link the material.

10. The method of claim 1 wherein the polymerisable material is contacted with the pharmaceutical particles or particle clusters simultaneously with the dye.

11. The method of claim 1 wherein the source of radiant energy is applied until a conformal coat of the desired thickness is formed around the pharmaceutical particles or particle clusters.

12. A microencapsulated pharmaceutical formulation as obtainable by the method of claim 1.

13. A microencapsulated pharmaceutical formulation comprising a microcapsule comprising a particulate pharmaceutical material conformally coated with a polymer coating covalently cross-linked by the action of an irradiated dye, wherein the dye is derivatized with phospholipid.

14. The formulation of claim 13 wherein the polymer coating is approximately 10 to 20 $\mu$m in thickness.

15. The formulation of claim 13 wherein the polymer provides an immuno-protective layer, while allowing therapeutic components from the particulate pharmaceutical material to exit the microcapsules.

16. The formulation of claim 15 wherein the particulate pharmaceutical material comprises cells or clusters of cells which produce and secrete a pharmaceutically active substance.

17. The formulation of claim 16 wherein the polymer is permeable to cell nutrients.

18. The formulation of claim 17 wherein the particulate pharmaceutical material comprises insulin secreting cells.

19. An implant for the therapeutic regulation of glucose comprising particles as obtainable by the method of claim 1.

20. The pharmaceutical formulation of any one of claims 13–18 wherein the dye is selected from the group consisting of eosin derivatized phospholipids or fluoroscein derivatized phospholipids.

* * * * *